United States Patent
Hopkins (10) Patent No.: US 6,862,794 B2
(45) Date of Patent: Mar. 8, 2005

(54) METHOD FOR MANUFACTURING AN ENDOVASCULAR SUPPORT DEVICE

(75) Inventor: Darren M. Hopkins, Santa Rosa, CA (US)

(73) Assignee: Medtronic AVE, Inc., Santa Rosa, CA (US)

(*) Notice: Subject to any disclaimer, the term of this patent is extended or adjusted under 35 U.S.C. 154(b) by 199 days.

(21) Appl. No.: 10/382,320

(22) Filed: Mar. 3, 2003

(65) Prior Publication Data

US 2004/0172804 A1 Sep. 9, 2004

(51) Int. Cl.⁷ ................................................ B23P 13/00
(52) U.S. Cl. ........................... 29/557; 29/558; 623/1.15
(58) Field of Search ........................ 29/557, 558, 26 A, 29/564.8, 417, 564; 623/1.15, 1.16, 1.49, 1.39

(56) References Cited

U.S. PATENT DOCUMENTS

| | | | |
|---|---|---|---|
| 5,780,807 A | 7/1998 | Saunders | |
| 5,817,152 A | 10/1998 | Birdsall et al. | |
| 5,836,965 A | 11/1998 | Jendersee et al. | |
| 5,843,117 A | * 12/1998 | Alt et al. | 623/1.15 |
| 6,027,526 A | * 2/2000 | Limon et al. | 623/1.15 |
| 6,146,417 A | * 11/2000 | Ischinger | 623/1.15 |
| 6,309,412 B1 | * 10/2001 | Lau et al. | 623/1.11 |
| 6,511,504 B1 | * 1/2003 | Lau et al. | 623/1.15 |
| 6,612,012 B2 | * 9/2003 | Mitelberg et al. | 29/447 |

FOREIGN PATENT DOCUMENTS

| | | |
|---|---|---|
| EP | 1 088 528 A1 | 4/2001 |
| EP | 1 266 637 A1 | 12/2002 |
| WO | WO/01/89420 A2 | 11/2001 |

* cited by examiner

Primary Examiner—David P. Bryant
Assistant Examiner—Jermie E. Cozart
(74) Attorney, Agent, or Firm—Ingrassia Fisher & Lorenz PC (57) ABSTRACT

A method of manufacturing an endovascular support device comprises providing a generally tubular member of an implantable material having a first, generally cylindrical outer surface and a second, generally cylindrical inner surface. At least a portion of the outer and inner surfaces of the tubular member are shaped in such a way to form a plurality of generally circular edgeless ring regions. Adjacent ring regions are connected together by one of a plurality of connecting regions. Openings are produced in the connecting regions in accordance with a predetermined pattern, and the generally tubular member is longitudinally expanded to form the support device.

23 Claims, 5 Drawing Sheets

METHOD FOR MANUFACTURING AN ENDOVASCULAR SUPPORT DEVICE

TECHNICAL FIELD

This invention relates generally to an endovascular support apparatus and, more particularly, to an improved method for the manufacture of a low-profile, edgeless geometry stent.

BACKGROUND OF THE INVENTION

Cardiovascular disease is a leading cause of death, and as a result, the medical community has devised various methods and devices for the treatment of coronary heart disease. One such treatment utilized in cases involving atherosclerosis and/or other forms of coronary narrowing is referred to a percutaneous transluminal coronary angioplasty, sometimes simply referred to as angioplasty or PTCA. The objective of this technique is to radially enlarge the lumen of an impacted artery. This is accomplished by first positioning an expandable balloon in a target lesion (i.e., the narrowed lumen of the coronary artery) and then inflating it. Inflation of the balloon enlarges the lumen by causing (1) soft or fatty plaque deposits to be flattened and (2) hardened deposits to crack and split. In addition, the artery wall itself is stretched by the inflated balloon.

In a typical percutaneous transluminal coronary angioplasty (PTCA) procedure, a hollow guiding catheter is introduced into the cardiovascular system of a patient via a relatively large vessel such as the femoral artery in the groin area or the brachial artery in the arm. After access to the patient's cardiovascular system has been achieved, a short hollow sheath is inserted to provide a passageway during the procedure. After the guiding catheter is directed to the ostium of the coronary artery to be treated by angioplasty, a flexible guide wire and a dilatation catheter having a balloon on the distal end thereof are introduced into the guide catheter with the guide wire sliding through the dilatation catheter. The guide wire is advanced to a target lesion in the vasculature. A balloon or dilatation catheter (made of, for example, polyethylene, polyethylene terathalate, PEBAX (polyamide block copolymers and polyester block copolymers), polyvinyl chloride, polyolefin, nylon or other suitable substance) is then slidably advanced over the previously advanced guide wire until properly positioned across the target lesion. Radiopaque markers in the balloon portion of the dilatation catheter assist in the positioning of the balloon across the lesion. After proper positioning, the balloon is inflated (e.g. generally with a contrast material to permit fluoroscopic viewing during the treatment) to enlarge the lumen of the artery. Treatment may require that the balloon be alternately inflated and deflated until satisfactory enlargement has been achieved. Lastly, the balloon is deflated to a small profile so that the dilatation catheter may be withdrawn from the patient's vasculature, and blood flow may resume through the dilated artery. Unfortunately, after angioplasty procedures of this type, there may occur a restenosis of the artery; i.e. a renarrowing of the treated coronary artery that significantly diminishes any positive results of the angioplasty procedure. In the past, restenosis frequently necessitated additional PTCA procedures or even more drastic open-heart surgery.

To prevent restenosis and strengthen the target area, various devices have been proposed for mechanically keeping the affected vessel open after completion of the angioplasty procedure. Such mechanical endoprosthetic devices, generally referred to as stents, are typically inserted into the vessel, positioned across the target lesion, and then expanded and/or implanted to first increase and then maintain the diameter of the lumen. A stent is typically mounted in a compressed state around a deflated balloon, and the balloon/stent assembly maneuvered through a patient's vasculature to the site of a target lesion. Once in place, the balloon is inflated causing expansion of the stent to a larger diameter for placement and implantation in the vasculature. In general, such endoprosthetic devices effectively overcome restenosis, thereby permitting and maintaining an increased flow of blood through a vessel.

Ideally, a stent should be relatively flexible to facilitate delivery (e.g. through torturous body lumens) and radially stable such that when expanded, the lumen receives adequate support to maintain its appropriate diameter. Stents may include a plurality of axial bends or crowns adjoined together by a plurality of struts so as to form a plurality of U-shaped members which are, in turn, coupled together. Additionally, stents may be formed from an implantable biocompatible material (e.g. stainless steel, titanium, tantalum, super-elastic nickel-titanium alloys, high-strength thermoplastic polymers, etc.).

Stents may be manufactured by means of a number of different methods involving wire, ring regions, torroids, or tubes. One method of cutting tubing to produce a desired pattern is shown and described in U.S. Pat. No. 5,780,807 issued Jul. 14, 1998, and entitled "Method and Apparatus for Direct Laser-Cutting of Metal Stents", the teaching of which are hereby incorporated by reference. This patent describes a method of producing a stent wherein a desired pattern is cut into the tubing by means of a machine controlled laser.

The tubing is fixed in a rotatable collet fixture of a machine-controlled laser apparatus so as to position the tubing relative to the laser beam. The tubing is then rotated and moved longitudinally relative to the laser in accordance with a predefined set of machine-encoded instructions. In this manner, the laser selectively removes material from the tubing by ablation, thus cutting a desired pattern into the tube and forming the stent.

Unfortunately, conventional laser-cutting methods such as the one mentioned above produce edges which are essentially perpendicular to the axis of the laser beam. Thus, cross-sections of stents produced in this manner are substantially square or rectangular. This is problematic because the resulting edges make insertion and manipulation of the stent more difficult and increase the likelihood of trauma to the patient's vasculature. Conversely, a stent comprised of fine geometries (e.g. narrow cuts and rounded edges) is easier to insert/manipulate minimizing risk to a patient. The edges produced by direct laser-cutting may be smoothed by electrochemically polishing the stent in an acidic aqueous bath (e.g. comprised of sulfuric acid, carboxylic acids, phosphates, corrosion inhibitors, and a biodegradable surface-active agent) at temperatures of approximately 110° Fahrenheit to 135° Fahrenheit. Unfortunately, such electropolishing processes present certain problems. For example, such techniques are generally cumbersome and messy. Furthermore, such processes are difficult to control resulting in lack of product consistency (e.g. stent-to-stent variations in stent element cross-section).

Segmented or modular stents have mitigated some of the problems associated with prior art stents; e.g. inability to conform to vessel shape, lack of sufficient flexibility for advancing through and implantation in vascular anatomy, etc. One such modular stent is shown and described in U.S.

Pat. No. 5,817,152 issued Oct. 6, 1998 and entitled "Connected Stent Apparatus", the teachings of which are hereby incorporated by reference. In this case, a single stent is comprised of at least two shorter stent segments which are connected, for example, by welding so as to produce a stent tailored to the length of the stenosis to be treated. Such stent segments may be produced from a machined wire ring or torroid (e.g. machined from stainless steel bar stock) which is then bent or formed into a desired shape, perhaps through the use of a forming tool. Unfortunately, since the diameter of the wire and the inner and outer diameters of the wire ring or torroid must be very precise and since the rings or torroids are typically produced one at a time, the machining process is difficult, time-consuming, and costly.

It should therefore be appreciated that it would be desirable to provide an improved method for the manufacture of a stent wherein the number of processing steps and overall production costs are reduced while maintaining the radial strength, flexibility, and edgeless geometry of the stent.

SUMMARY OF THE INVENTION

According to a first aspect of the invention, there is provided a method manufacturing an endovascular support device, which comprises providing a generally tubular member of an implantable material having a first, generally cylindrical outer surface and a second, generally cylindrical inner surface. At least a portion of the outer and inner surfaces of the tubular member are shaped in such a way as to form a plurality of generally circular edgeless ring regions. Adjacent ring regions are connected together by one of a plurality of connecting regions. Openings are then produced in the connecting regions in accordance with a predetermined pattern, and the generally tubular member is longitudinally expanded to form the support device.

BRIEF DESCRIPTION OF THE DRAWINGS

The following drawings are illustrative of particular embodiments and therefore do not limit the scope of the invention, but are presented to assist in providing a proper understanding. The drawings are not to scale (unless so stated) and are intended for use in conjunction with the explanations of the following detailed description. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
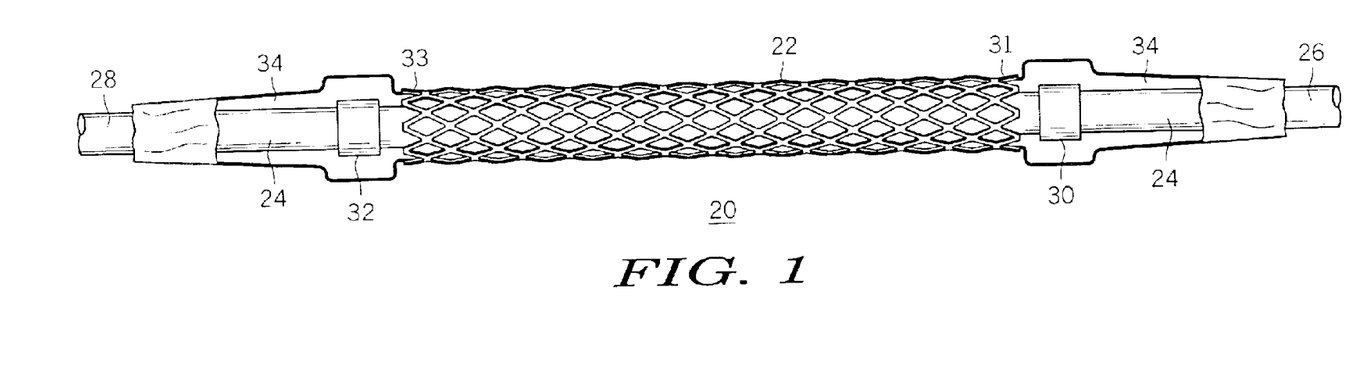
FIG. 1 is a longitudinal view, partially in cross-section, of a conventional balloon/stent assembly.

FIG. 1 is a longitudinal, cross-sectional view of a balloon/stent delivery system or assembly comprising an endovascular support device such as a stent 22 having distal edge 31, proximal edge 33, and an opening therethrough, an inner member or wire lumen 24 having a distal end 26 and a proximal end 28, and distal and proximal radiopaque marker bands 30 and 32 respectively positioned on inner member or wire lumen 24 (i.e. near the distal and proximal ends of stent 22). It will be recognized by those skilled in the art that inner member or guide lumen 24 is configured for the insertion of a conventional guide wire (not shown) which will enable the balloon/stent assembly to be guided to and positioned at a target location.

Any conventional or modified balloon catheter device may be used such as a PTCA balloon catheter. An expandable balloon portion 34 is mounted on inner member 24 in a compressed or collapsed state beneath stent 22 and extends beyond the proximal and distal ends of stent 22. Balloon 34 is generally made of a pliable material such as polyethylene, polyethylene terathalate, PEBAX (polyamide block copolymers and polyester block copolymers), polyvinyl chloride, polyolefin, nylon or the like. The length and the diameter of the balloon may be selected to accommodate the particular configuration of the stent to be deployed. Stent 22 may be constructed of any implantable material having good mechanical strength, such as stainless steel, titanium, tantalum, super-elastic nickel-titanium alloys, or high-strength thermoplastic polymers. The outside or wall of stent 22 may be selectively plated with platinum or other implantable radiopaque substance to provide visibility during fluoroscopy. The cross-sectional shape of the tubular finished stent 22 may be circular, ellipsoidal, rectangular, hexagonal, square, or any other desired shape, although a circular or ellipsoidal cross-section is preferable. The length and width of stent 22 is generally determined to a large degree by the size of the vessel into which the stent will be deployed. Stent 22 must be of sufficient length to extend across a significant portion of the target area and to maintain its axial orientation (e.g. resist shifting under the hydraulics of blood flow) while, at the same time, not be unnecessarily long so as to result in the introduction of an unnecessarily large amount of material into the vessel.

After stent selection, stent 22 is compressed upon the outside of balloon 34. An inner sheath (not shown) is placed over each end of balloon 34 and an exterior sheath (also not shown), is placed over the ends of the interior sheath so as to cover stent 22 and overlap with the interior sheaths. The assembly is then pressurized by introducing air or an inert gas such as nitrogen through the lumen 24 into the interior of balloon 34 thereby expanding the balloon within the sheaths. The assembly is then exposed to an elevated temperature while the pressure within the balloon is held relatively constant. The temperature may be, for example, approximately 150 degrees Fahrenheit and the pressure approximately 70 psi. Following heating, the balloon/stent assembly is allowed to cool within the sheaths, setting the shape of balloon 34. The sheaths may then be removed. This process is described in detail in U.S. Pat. No. 5,836,965 entitled "Stent Delivery and Deployment Method" issued Nov. 17, 1998, the teachings of which are hereby incorporated by reference.

Marker bands 30 and 32, which may be viewed through fluoroscopy, assist in positioning the assembly. When the assembly is properly located across a lesion, the balloon may be inflated. This results in the generally uniform, symmetrical expansion of the stent and balloon. The amount of inflation, and thus the amount of expansion of the stent, may be varied as dictated by the lesion itself As stated previously, prior art endovascular support devices may be produced by precision machining a wire ring having a substantially circular cross-section from stainless steel bar stock wherein the ring is bent or formed into a desired shape (e.g. through the use of a forming tool). However, this method is both time consuming and costly because each ring is cut individually and has very precise inner and outer diameters and a very precise wire cross-section. As also stated previously, prior arts stents have also been produced via a laser-cutting process wherein a desired pattern is cut into tubing by means of a machine-controlled laser. In this case, the tubing may be fixed in a rotatable collet fixture relative to a machine-controlled laser, which laser-cuts the tubing in accordance with a predetermined pattern to form the discrete pattern of the finished stent. Unfortunately, as does precision machining, this method has several disadvantages. For example, additional steps should be taken to round the square/rectangular cross-sections of stent elements produced by direct laser cutting. Such steps are generally cumbersome, messy, and difficult to control. As described hereinafter, the inventive process mitigates these problems through a hybrid process involving both machining and laser-cutting.

Figure 2:
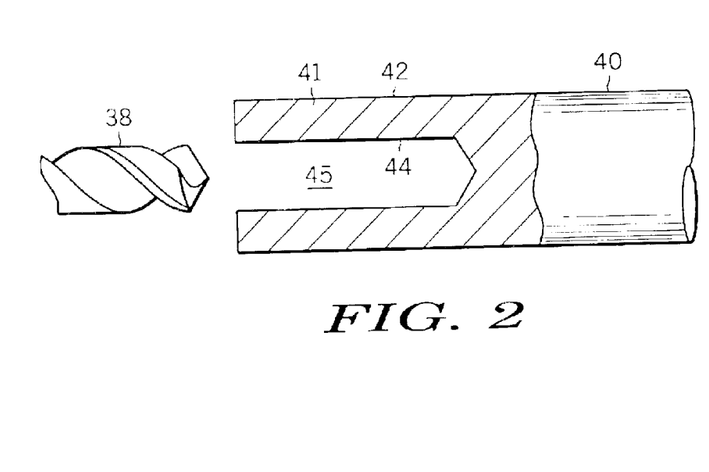
FIG. 2 is a longitudinal view, partially in cross-section, of a generally tubular member in a working relationship with a drilling apparatus.

FIG. 2 is a longitudinal view, partially in cross-section, of a generally tubular member 40 situated in a working relationship with a drilling apparatus 38 and having an outer surface 42. As is represented at step 110 in FIG. 11, drilling apparatus 38 (e.g. a carbide drill bit) is made to engage cylindrical member 40 so as to create a generally cylindrical cavity 45 having an inner surface 44. The diameter of cavity 45 is chosen so as to produce a wall 41 having a thickness suitable for stent formation. For example, cavity 45 may extend approximately 0.063 inch into member 40, and have an inner diameter (ID) of approximately 0.48 inch. Member 40 may be machined from any suitable bar-stock implantable material (e.g. nickel-titanium, stainless steel, etc.) and have an outer diameter suitable for stent formation (e.g. approximately 0.5 inch).

Figure 3:
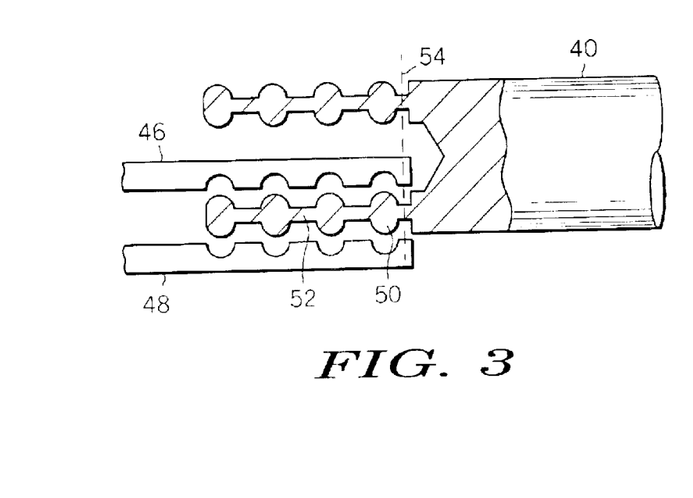
FIG. 3 is a longitudinal view, partially in cross-section, of the generally tubular member of FIG. 2 in a working relationship with inner and outer shaping tools.
Figure 7:
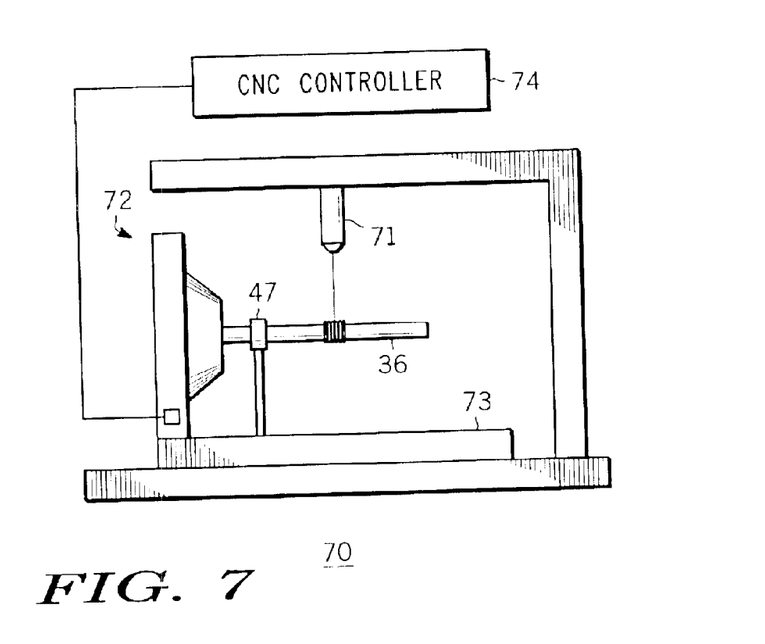
FIG. 7 is a schematic representation of an apparatus for selective laser-cutting.
Figure 11:
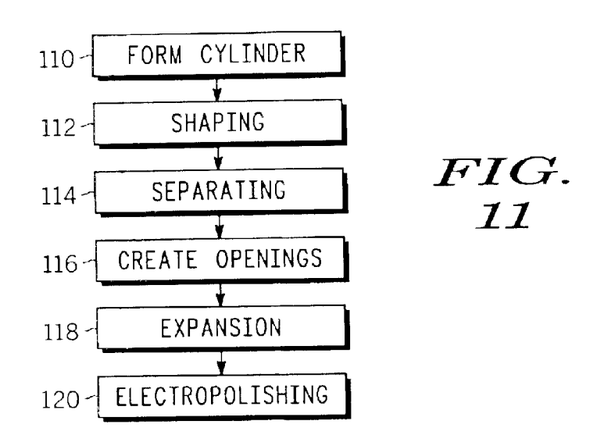
FIG. 11 is a process flow-chart describing the production of a stent in accordance with the teachings of the present invention.
Figure 12:
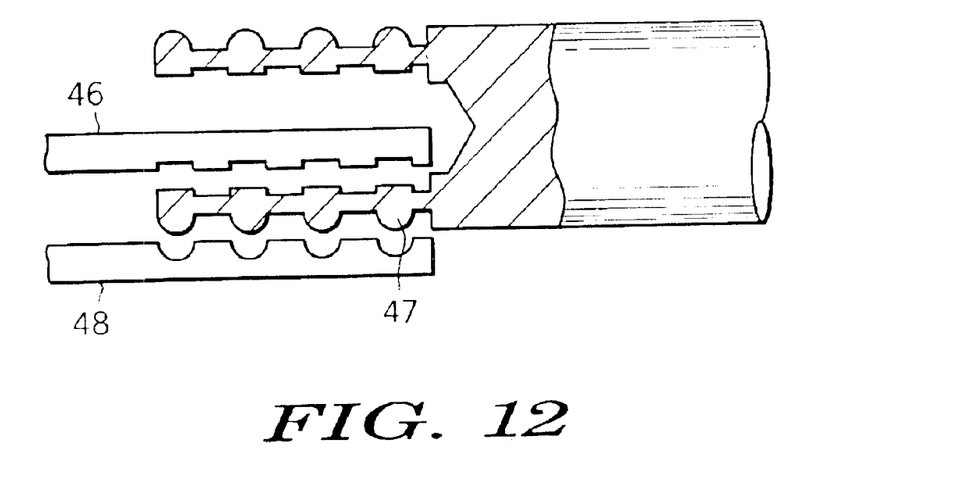
FIGS. 12 and 13 illustrate alternate inner and outer shaping tools.
Figure 13:
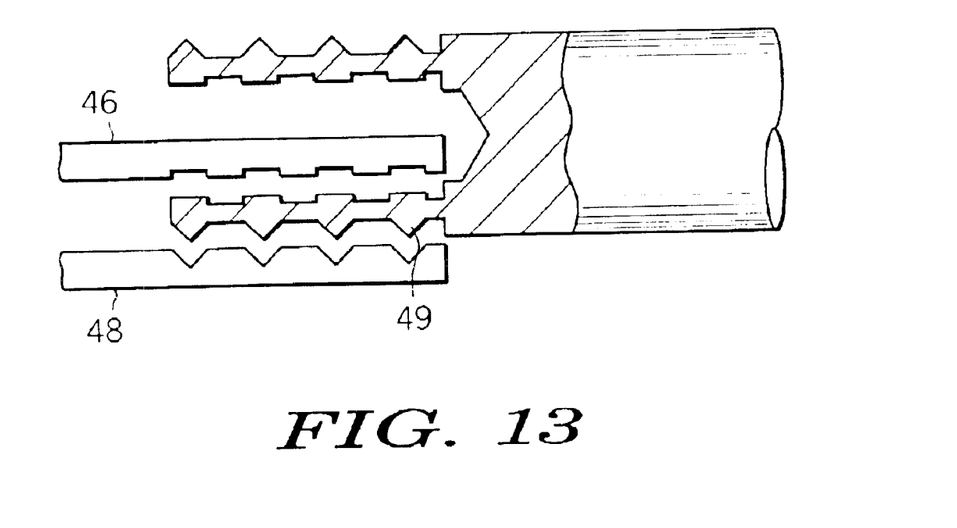

Next, as is represented at step 112 in FIG. 11, a portion of outer surface 42 and an opposite portion of inner surface 44 are shaped so as to form a plurality of generally circular edgeless ring regions 50 and a plurality of connecting regions 52 as is shown in FIG. 3. As can be seen, adjacent ring regions 50 are connected by one of the plurality connecting regions 52. It should be appreciated that the dimensions, arrangement, and number of ring regions 50 and connecting or web regions 52 may be determined by the profile of shaping tools 46 and 48 (i.e. the profile of the cutting edges) to suit a particular application. That is, the shapes imparted on outer surface 42 and inner surface 44 will generally contour the respective cutting edges of shaping tools 48 and 46, which may be made of, for example, carbide. Shaping tools 46 and 48 contact and exert cutting forces against inner surface 44 and outer surface 42, respectively. Member 40 may then be rotated relative to shaping tools 46 and 48 (e.g. via rotary collet 72 as depicted in FIG. 7) so as to shape inner surface 44 and outer surface 42, either sequentially or simultaneously. Shaping tools 46 and 48 may be incorporated into a computer numerically controlled (CNC) X/Y table (as may be drilling apparatus 38) to partially or fully automate the process and help ensure accuracy, consistency, and efficiency. Furthermore, if desired to meet the requirements of a particular application, shaping tools 46 and 48 may be configured to provide ring region cross-sections of various shapes. For example, the shaping tools shown in FIGS. 12 and 13 produce substantially semicircular and substantially triangular regions 47 and 49 respectively.

Figure 4:
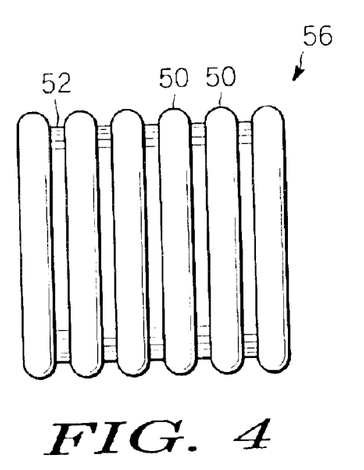
FIG. 4 is a longitudinal view of a section of a generally tubular member; shaped in accordance with the present invention.
Figure 5:
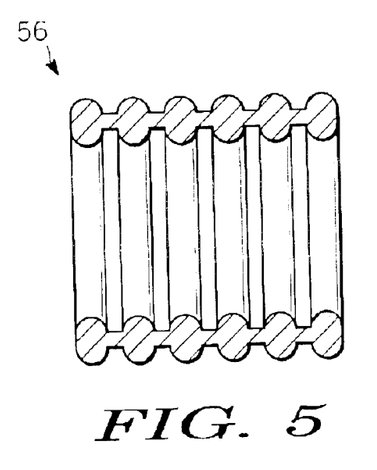
FIG. 5 is a cross-sectional view of the tubular member shown in FIG. 4.

As represented at step 114 of FIG. 11, after shaping, the shaped portion of tubular member 40 or a portion thereof may be cleaved as, for example, by means of a carbide cutting tool or saw so as to form segment 56 shown in FIG. 4 and in cross-section in FIG. 5. This incision is generally perpendicular to the longitudinal axis of tubular member 40. The length of segment 56 (e.g. 0.063 inch) may be selected to accommodate the particular configuration of the stent to be formed.

In step 116 of FIG. 11, a plurality of openings 60 (FIG. 6) are created in connecting regions 52 of segment 56 in accordance with a predetermined pattern. This may be accomplished by, for example, a laser-cutting apparatus 70 of the type shown schematically in FIG. 7 and in greater detail in FIG. 8. Laser-cutting apparatus 70 may be computer numerically controlled (CNC) so as to selectively create openings 60. Referring to FIG. 7, segment 56 may be placed on a support rod 36 which in turn is secured in a rotatable collet fixture 72 of a machine-controlled (CNC) laser-cutting apparatus 70 which functions to position segment 56 relative to a laser 71. As stated previously, this may be accomplished by using a CNC opposing collet fixture which allows for axial rotation of segment 56 in conjunction with an X/Y table 73. X/Y table 73 moves segment 56 relative to laser 71. The laser-cutting process may be controlled by means of a precision CNC controller 74, for example of the type manufactured and sold by Anorad Corporation.

Figure 8:
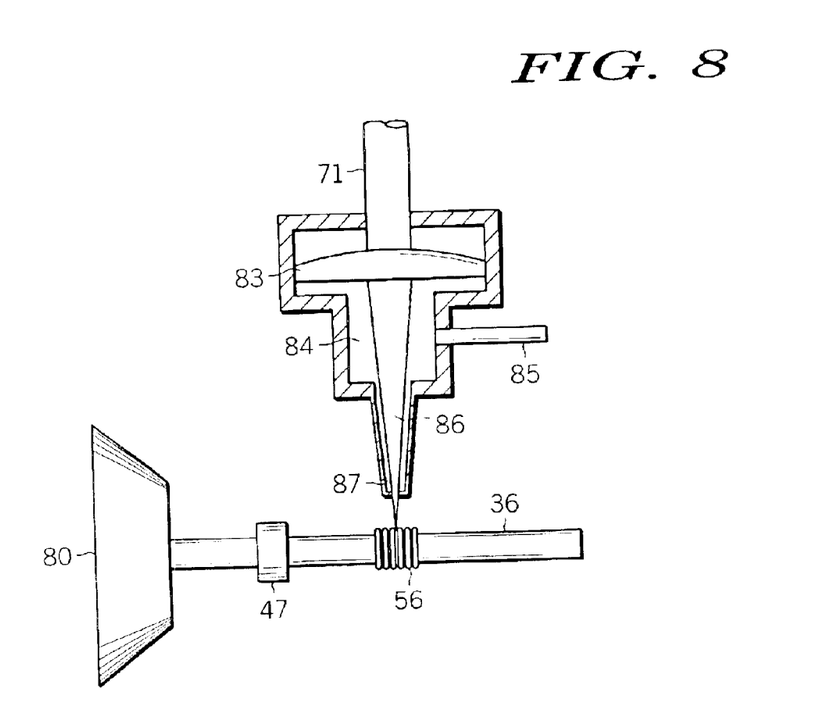
FIG. 8 is a more detailed view of the laser-cutting apparatus shown in FIG. 7.

FIG. 8 is a more detailed view of the laser-cutting apparatus shown in FIG. 7. As can be seen, segment 56 is positioned on rod 36 which is secured in CNC controlled rotary collet 80. Laser beam 71 is passed through a focusing lens 83 which is, in turn, surrounded by a coaxial gas jet assembly 84 having a gas input 85. In this manner, the gas stream that surrounds the focused laser beam 86 is directed along the laser beam axis to a coaxial gas jet nozzle 87. The gas jet (e.g. oxygen) reacts with segment 56 to assist in the cutting process. Focused laser beam 86 acts as an ignition source and controls the reaction of the oxygen with the metal in order to produce high-precision cuts in segment 56.

Figure 6:
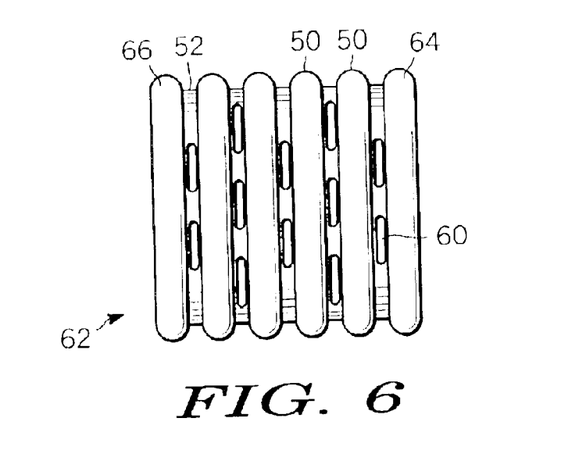
FIG. 6 is a longitudinal view of the tubular member section shown in FIG. 4 after undergoing a cutting process in accordance with the teachings of the present invention.

Thus, utilizing laser-cutting apparatus 70, openings 60 (FIG. 6) are selectively cut in connecting regions 52 of stent segment 62 in accordance with a predetermined pattern. This predetermined pattern may be radially symmetrical, linearly symmetrical, or unsymmetrical. FIG. 6 is a longitudinal view of stent segment 56 after undergoing laser-cutting as described above to form cut stent segment 62. It should be appreciated that, although openings 60 have been described as being produced by means of a laser cutting apparatus 70, openings 60 may be made utilizing other known techniques (e.g. etching).

Figure 9:
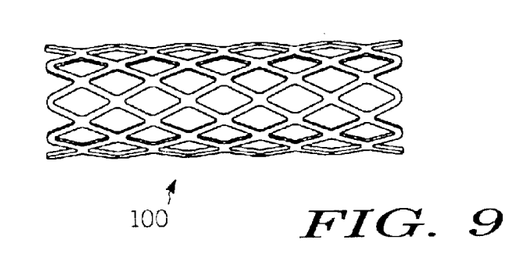
FIG. 9 is a longitudinal view of the tubular member shown in FIG. 6 after expansion.
Figure 10:
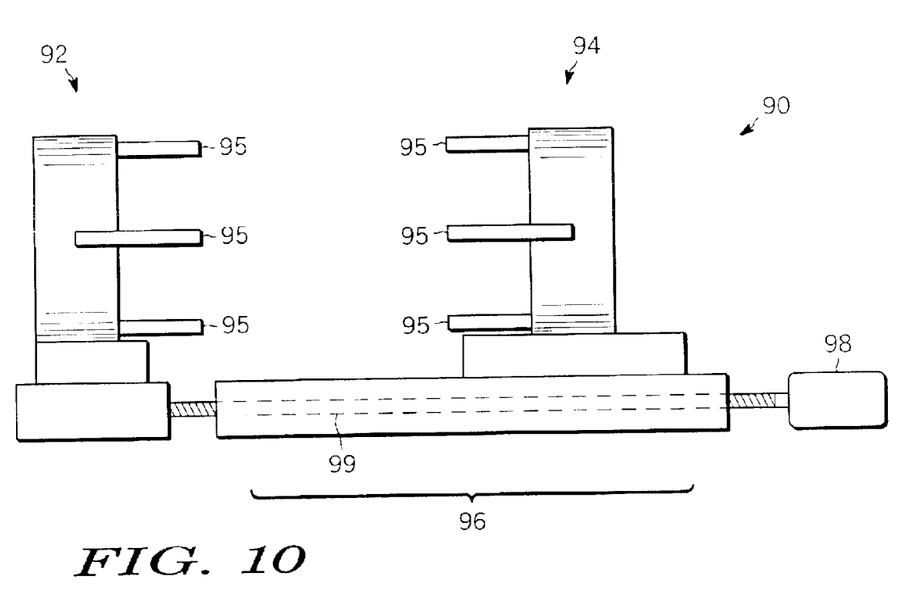
FIG. 10 is a schematic representation of a stent expansion device.

Next, as is represented at step 118 in FIG. 11, cut stent segment 62 is longitudinally expanded to form expanded stent 100 as is shown in FIG. 9. It may be desirable to soften segment 62 prior to expansion through annealing. For example, flash-annealing may be performed in a vacuum furnace at a temperature of approximately 1,110° C. Referring again to FIG. 6, it can be seen that segment 62, having an opening 60 therein has a proximal end 66 and distal end 64. Elongation may be performed by any apparatus, mechanical or otherwise, capable of grasping proximal end 66 and distal end 64 and exerting sufficient force to cause longitudinal expansion of cut stent segment 62. One such expansion device 90 is depicted in FIG. 10 and includes track 96, motor 98, and gripping members 92 and 94. As can be seen, gripping member 94 moves longitudinally relative to gripping member 92 along track 96. That is, motor 98 acts to impart rotary motion to a lead screw 99 which drives gripping member 94. To perform expansion, cut stent segment 62 is placed in puller device 90 such that gripping members 92 and 94 may each secure to an end of cut stent segment 62 (e.g. by means of clamps on gripping fingers 95). Gripping member 94 is then driven by motor 98 away from gripping member 92 thereby elongating cut stent segment 62. After sufficient expansion, cut stent segment 62 appears as is shown at 100 in FIG. 9. As can be seen, finished stent 100 has a scaffold-like structure. Lastly, as represented at step 120 in FIG. 11, finished stent 100 may undergo a conventional electropolishing step for improving corrosion resistance. For example, if finished stent 100 is comprised of stainless steel, electropolishing will attract chrome to the surface of the metal. If desired, finished stent 100 may undergo a final step of tumbling to remove possible impurities (i.e. slag) created during the laser-cutting process. Thus, there has been provided a method of manufacturing an endovascular support device which combines machining steps and laser-cutting so as to reduce the number of processing steps and overall production costs while maintaining strength, flexibility, and an edgeless geometry.

In the foregoing specification, the invention has been described with reference to a specific embodiment. However, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

What is claimed is:

1. A method of manufacturing an endovascular support device, comprising:
   providing a substantially tubular member of an implantable material having a first, substantially cylindrical outer surface and a second, substantially cylindrical inner surface;
   shaping at least a portion of said outer surface and said inner surface so as to form a plurality of generally circular, edgeless ring regions, adjacent ones of said ring regions connected by one of a plurality of connecting regions;
   producing at least one opening in selected ones of said connecting regions in accordance with a predetermined pattern; and
   longitudinally expanding said at least a portion of said substantially tubular member to form said support device.

2. A method of manufacturing an endovascular support device according to claim 1 wherein said producing at least one opening comprises producing a plurality of openings.

3. A method of manufacturing an endovascular support device according to claim 2 wherein said plurality of openings is substantially symmetrical.

4. A method of manufacturing an endovascular support device according to claim 2 wherein said producing a plurality of openings in selected ones of said connecting regions comprises laser-cutting.

5. A method of manufacturing an endovascular support device according to claim 4 wherein said laser-cutting is computer numerically controlled.

6. A method of manufacturing an endovascular support device according to claim 1 wherein said implantable material is stainless steel.

7. A method of manufacturing an endovascular support device according to claim 1 wherein said implantable material is nickel-titanium.

8. A method of manufacturing an endovascular support device according to claim 1 wherein said tubular member has an outer diameter of approximately 0.5 inch.

9. A method of manufacturing an endovascular support device according to claim 8 wherein said second, generally cylindrical inner surface has a diameter of approximately 0.48 inch.

10. A method of manufacturing an endovascular support device according to claim 1 wherein said shaping comprises cutting said inner surface and said outer surface with at least one shaping tool.

11. A method of manufacturing an endovascular support device according to claim 10 wherein said cutting comprises rotating said substantially tubular member relative to said at least one shaping tool.

12. A method of manufacturing an endovascular support device according to claim 11 wherein said at least one shaping tool is computer numerically controlled.

13. A method of manufacturing an endovascular support device according to claim 1 further comprising separating said portion from said substantially tubular member after shaping.

14. A method of manufacturing an endovascular support device according to claim 13 wherein said separating comprises cutting said portion from said substantially tubular member.

15. A method of manufacturing an endovascular support device according to claim 1 wherein said providing, said substantially tubular member comprises axially drilling a cylinder of said implantable metal.

16. A method of manufacturing an endovascular support device according to claim 1 further comprising annealing said substantially tubular member prior to expanding.

17. A method of manufacturing an endovascular support device according to claim 1 further comprising electropolishing said substantially tubular member after expanding.

18. A method of manufacturing an endovascular support device, comprising:
   providing a substantially tubular member of implantable material having a first, substantially cylindrical outer surface and a second, substantially cylindrical inner surface;
   machining said outer surface and said inner surface to form a plurality of ring regions, adjacent ones of which are connected by connecting regions;

laser-cutting a predetermined pattern of openings in said connecting regions; and longitudinally expanding said substantially tubular member to form said support device.

19. A method of manufacturing an endovascular support device according to claim 18 wherein said machining comprises cutting said inner surface and said outer surface with at least one shaping tool.

20. A method of manufacturing an endovascular support device according to claim 19 wherein said cutting comprises:

contacting said inner surface and said outer surface with said at least one shaping tool; and rotating said substantially tubular member relative to said at least one shaping tool.

21. A method of manufacturing an endovascular support device according to claim 20 wherein said providing said substantially tubular member comprises axially boring a cylinder of said implantable metal.

22. A method of manufacturing an endovascular support device according to claim 21 wherein further comprising annealing said substantially tubular member prior to expanding.

23. A method of manufacturing an endovascular support device according to claim 22 wherein further comprising electropolishing said substantially tubular member after expanding.

* * * * *